United States Patent [19]

Wiegand et al.

[11] Patent Number: 4,870,191

[45] Date of Patent: Sep. 26, 1989

[54] SILICON CONTAINING REACTION PRODUCT

[75] Inventors: Karl E. Wiegand; Patrick C. Hu, both of Baton Rouge, La.

[73] Assignee: Ethyl Corporation, Richmond, Va.

[21] Appl. No.: 223,010

[22] Filed: Jul. 22, 1988

[51] Int. Cl.$^4$ .......................................... C07D 307/32
[52] U.S. Cl. .................................... 549/214; 549/315
[58] Field of Search ............................... 549/214, 315

[56]  References Cited
FOREIGN PATENT DOCUMENTS 285285  3/1914  Fed. Rep. of Germany .

Primary Examiner—Glennon H. Hollrah
Assistant Examiner—Ba Trinh
Attorney, Agent, or Firm—John F. Sieberth; Robert J. Baran

[57] ABSTRACT

Ascorbic acid and substituted ascorbic acids can be reacted with a tetraorganosilicate such as a tetraalkylorthosilicate to yield a product which contains silicon. The products are generally solid in nature, and typically they are insoluble without hydrolysis. The products are useful as active agents in the prevention, treatment, or delaying of the onset of calcium-related bone disease such as post-menopausal osteoporosis.

5 Claims, No Drawings

SILICON CONTAINING REACTION PRODUCT

Field of the Invention

This invention pertains to silicon-containing reaction products of ascorbic acid and substituted ascorbic acids. This invention also relates to the use of the reaction products in the treatment of bone disease.

BACKGROUND

Silicon containing reaction products of orthosilicic acid esters and certain polyhydroxy compounds are known, German Patent No. 285,285.

SUMMARY OF THE INVENTION

This invention relates to silicon-containing reaction products produced by reacting a silicate ester with ascorbic acid or a related compound. This invention also relates to the use of the above-described reaction products in the treatment or prevention of calcium related bone disorders. Also, this invention relates to use of the reaction products to increase the bone strength or bone mass of an animal having a bone strength or bone mass less than desired. Among other utilities, the reaction products of this invention can be used to treat, prevent or delay post-menopausal osteoporosis in human females.

The products of this invention are made by contacting the ascorbic acid compound with the silicate ester, under reaction conditions which facilitate transesterification. For example, the reaction of ascorbic acid with tetraethylorthosilicate, $Si(OC_2H_5)_4$, results in the replacement of from one to four ethoxy radicals (per silicon atom) with radical(s) derived from ascorbic acid. Thus, the products of the reaction of ascorbic acid and $SiOC_2H_5)_4$ are a silicon-containing derivative of ascorbic acid. To facilitate the preparative process, the reaction temperature employed is above ambient; such reaction temperatures assist removal of the ethanol by-product from the reaction zone, and help drive the reaction to a desired degree of completion.

In one preferred embodiment, this invention comprises the use of silicic acid produced—from one or more of the aforementioned therapeutic agents—by a warm blooded, vertebrate animal being treated with said therapeutic agent or agents. The silicic acid can be produced in the gastrointestinal tract, or in the gastrointestinal mucosa, or at any other site within the animal being treated. The silicic acid produced in this way can be used (a) to treat, prevent, or delay the onset of calcium-related bone disease, or (b) to increase the strength of bone in an animal having a bone strength less than desired. Like the aforementioned therapeutic agents, the silicic acid produced by the subject being treated with the aforementioned therapeutic agents can treat, prevent, or delay the onset of post-menopausal osteoporosis in human females, or steroid-induced osteoporosis, or hypogonadotropic osteoporosis in human males or females.

The site and degree of hydrolysis which occurs with the therapeutic agents of this invention may also serve to alter their specific activities, directing them to systemic locations not typically available to free silicic acid, thereby allowing interaction with new or additional active sites. Thus, not only the parent compounds, but all metabolites thereof, including silicic acid itself, may be involved in particular bone growth or regrowth stimulatory activity of interest here. We thus recognize that a complex set of transformations in these compounds is expected, and any or several transformation products can be responsible for different spectra of activity or utility.

DESCRIPTION OF PREFERRED EMBODIMENTS

Ascorbic acid has the formula:

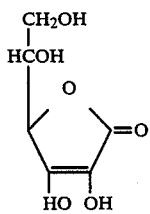

It is a preferred starting material for preparing the products of this invention. Substituted ascorbic acids can also be used as starting materials. For the purpose of this invention, the term "substituted ascorbic acids" means those compounds which have the ascorbic acid structure depicted above, with one or more replaceable hydrogens substituted with an organic radical. To be useful as starting materials, the substituted ascorbic acids must have at least one replaceable hydrogen (e.g. a hydrogen in an —OH group) which is reactable with the silicate ester under the reaction conditions employed.

The organo groups which may be present as substituents in the substituted ascorbic acid can be hydrocarbyl groups, i.e. groups that are solely composed of carbon and hydrogen. Preferably, the hydrocarbyl groups are alkyl radicals; more preferably, lower alkyl radicals. For the purpose of this invention, "lower alkyl radicals" are alkyl radicals having up to about 6 carbon atoms. Straight or branched chain alkyl radicals may be present as substituents on the ascorbic acid moiety, and are included in the term "lower alkyl radicals". Examples of such radicals are methyl, ethyl, n-propyl, sec-butyl, n-pentyl, n-hexyl, and the like.

It is to be understood, however, that the nature and size of the organo substituents (which may be bonded to the ascorbic acid moiety) may have modifying effects, but are not critical so long as they are physiologically acceptable. For the purpose of this invention, "physiologically acceptable" means that the organo substituent is not so toxic as to make the use of the silicon compound provided by this invention unacceptable as a therapeutic agent. Preferably, the groups can be added to the ascorbic acid structure at an acceptable cost. Stated another way, it is preferred that the substituent groups be relatively inexpensive. Also, it is preferred that the organo substituents be of a size, nature, and configuration that they do not hinder the desired reaction by steric hindrance, or by causing an unacceptable amount of extraneous side reaction(s). In addition to the hydrocarbyl groups described above, other physiologically acceptable substituents can be present in the ascorbic acid derivative. Such substituents are illustrated by acyl, aryl, aralkyl, alkaryl, heterocyclic alkyl, sulfonyl, alkylsulfonyl, arylsulfonyl, alkylphosphato, carbonyl, thiocarbonyl, and the like.

There is no real upper limit on the number of organic substituents which can be bonded to the ascorbic acid moiety, provided that there is at least one reactable hydrogen present. Generally speaking however, monosubstituted ascorbic acids are preferred over multi-substituted ascorbic acids. Thus, in a highly preferred embodiment, the ascorbic acid derivative used as a starting material for preparing products of this invention contains from 6 to about 12 carbon atoms.

As indicated above, the products of this invention are prepared by reacting ascorbic acid, or a substituted ascorbic acid, or a mixture of such materials, with a silicate ester. Preferred silicate esters are the orthosilicates; i.e. compounds having the formula $Si(OR)_4$, wherein R is an organo radical. In this formula, the radicals may be alike or different. Preferably, all four organo radicals in the orthosilicate starting materials are the same. The exact nature, size and configuration of the organo radicals is not critical. However, it is preferred that the radicals do not hinder the preparative process by steric hindrance, or by causing an untoward, i.e. unacceptable, amount of undesirable side reaction(s). As with the ascorbic acid reactant, it is also preferred that the silicate ester used as a starting material be relatively inexpensive.

For these reasons, it is preferred that the radicals depicted by R in the above formula, be solely composed of carbon and hydrogen. More preferably, they are acylic. Most preferably, they are alkyl radicals. Straight or branched chain alkyl groups are suitable. Most preferably, the radicals depicted by R are alkyl radicals having 1 to about 6 carbon atoms, i.e. "lower alkyl radicals" as defined above. Examples of such radicals are methyl, ethyl, n-propyl, sec-butyl, n-pentyl, n-hexyl, and the like.

The preferred orthosilicates for use in this invention can contain from 4 carbon atoms (i.e. four methyl groups) up to about 24 carbons (four hexyl groups). A highly preferred tetraalkylorthosilicate starting material for this invention is tetraethylorthosilicate; $Si(OC_2H_5)_4$ To prepare the products of this invention, one or more ascorbic acid compounds are mixed with one or more silicate esters, and heated. Preferably, from 1 to 4 moles of ascorbic acid or substituted ascorbic acid are reacted per mole of silicate ester, or 1 to 4 moles of silicate ester are reacted per each mole of ascorbic acid or substituted ascorbic acid. Greater or lesser ratios can be used, but use of these ratios may entail the need to separate unreacted starting material from product.

The starting materials can be simply admixed and heated, or they can be reacted in the presence of an inert liquid reaction medium, such as a hydrocarbon.

In many instances, a liquid reaction medium is not needed. For example, at reaction temperatures ascorbic acid is soluble (to a usable extent) in tetraethylorthosilicate. On the other hand when both reactants are solids at reaction temperatures, a liquid reaction medium is preferably used. If the reactants are not completely soluble in the liquid, agitation, e.g. stirring, can be used to facilitate contacting the reactants.

The reaction temperature is selected to give a reasonable product yield within a reasonable time. Usually, temperatures above about 65° C. are employed. Temperatures as high as 200° C. or higher can be used.

Preferably, the reaction to prepare products of this invention is conducted at atmospheric pressure. When this expedient is used, it is preferred to use a reaction temperature which is below the boiling point of the lowest boiling reactant in the reaction mixture, and at a temperature which is above the boiling point of the by-product alcohol that is produced in the process. For example, when ascorbic acid is reacted with tetraethylorthosilicate, a convenient reaction temperature is about 155° C. That temperature is slightly below the boiling point of the silicate, and above the boiling point of the ethanol by-product. Such a temperature facilitates removal of unreacted tetraethylorthosilicate from the reaction zone, and thereby assists in isolation of the reaction product.

The reaction zone may be swept with a stream of inert gas if desired, to assist removal of co-product alcohol and/or unreacted starting material.

The reaction temperature is not a truly independent variable, but is at least somewhat dependent upon the other reaction conditions employed. In general, higher reaction temperatures afford shorter reaction times. Furthermore, good mixing of the reactants, and efficient removal of the alcohol co-product help drive the reaction to completion, and thereby lead to shorter reaction periods. In general, the process can be conducted over a reaction period of from about 1 to about 24 hours. The reaction can be conducted in a plurality of stages. For example, the reaction can be conducted at one temperature for an initial reaction period; and thereafter, the temperature can be increased somewhat for a relatively short time, in order to assist reaction of the portion of starting materials which remains after the initial reaction period.

As stated above, a preferred reaction pressure is ambient pressure. However, it will be apparent to a skilled practitioner that sub-atmospheric pressures and super-atmospheric pressures ca be employed if desired.

Usually, the products are solid in nature. When a liquid is present in the reaction mixture, the products can be removed therefrom by filtration. Preferably, the reactant mixture is cooled prior to filtering the product. After the product is isolated from the reaction mixture, it can be washed, dried, and subdivided, if desired.

In a preferred embodiment, the starting materials are combined and reacted such that the product of this invention contains at least about 2 weight percent, and more preferably from about 10 to about 15 weight percent silicon. Suitable products of this type can be made by reacting one mole of ascorbic acid with one mole of a tetraloweralkylorthosilicate, such a tetraethylorthosilicate.

The exact nature of the products of this invention is not known. Analysis of a typical product of this invention (by NMR and infrared) indicates that the reaction product is polymeric in nature. The molecular weight of the products, i.e. the degree of polymerization, is difficult to determine since the products are generally insoluble in solvents commonly used in molecular weight determinations. The products can be dissolved in an aqueous medium such as an aqueous acid or aqueous base. However, solution in an aqueous medium causes hydrolysis. Hence, the molecular weight of the products of this invention cannot be determined in aqueous media.

It is believed that the products of this invention are not homogeneous, but rather that they consist of mixtures of various materials made by reaction of the orthosilicate ester and the ascorbic acid and/or substituted ascorbic acid.

EXAMPLE

A three-necked, round-bottom, Pyrex flask fitted with a mechanical stirrer was employed. One neck was fitted with a condenser so that volatile materials could be retained or removed, as desired. To minimize undesired hydrolysis, a positive nitrogen pressure was employed to prevent moisture entering the system.

A 100 gram portion of ascorbic acid was added to the reaction flask. After mild heating and nitrogen purging, 200 ml of tetraethylorthosilicate was added. The resultant mixture was then heated to 50° C. for two hours, followed by another two hours at 80° C., under vigorous agitation. The resultant mixture was then heated to remove ethanol, and this was followed by tetraethylorthosilicate removal at about 155° C.

The solid product remaining in the flask was cooled to room temperature, and then washed with methanol. The sample was then dried overnight in a vacuum oven, and then subdivided by grinding in a Waring blender.

The product was insoluble or substantially insoluble in organic solvents such as dichloromethane, dimethylsulfoxide (DMSO), acetone, toluene, tetrahydrofuran (THF), and carbon tetrachloride.

The product contained 11 percent silicon as determined by ICP (inductively coupled plasma) atomic absorption spectrometry. Examination by XRD (X-ray diffraction) suggested the presence of ascorbic acid groups within the product. When the diffraction pattern of the product was compared to the diffraction pattern of starting ascorbic acid, an ascorbic acid content of 19 weight percent was determined.

To identify species produced by hydrolysis of the product, a small product sample was slurried in water, under agitation. At various time periods, slurries were withdrawn and filtered through a syringe filter. The siliceous material in the filtrate was then derivatized using hexamethyldisiloxane in the presence of HCl. The triethylsilyl derivative produced was analyzed by vapor phase chromatography. Results showed only the presence of the trimethylsilyl derivative of orthosilicic acid. This suggests that almost all siliceous material generated by hydrolysis of the sample was orthosilicic acid and/or species that can be converted to orthosilicic acid readily.

Another sample of the product was hydrolyzed under alkaline conditions to determine the amount of ethanol present. A release of ethanol equivalent to 5.8 weight percent of the sample was detected. This amount of ethanol is substantially smaller than the theoretical ethanol release obtained by hydrolysis of tetraethylorthosilicate (88.4 weight percent).

The above procedure can be modified by using a reaction temperature of from about 65° C. to about 200° C. The process can be further modified by using a substituted ascorbic acid, such as those defined above, e.g. ascorbic acid derivatives having an ascorbic acid moiety substituted with methyl, ethyl, n-propyl, sec-butyl, n-pentyl, or n-hexyl groups, or being partially esterified with carboxylic acid groups, such as formyl, acetyl, propionyl or caproyl groups.

The above procedure can be modified by replacing the tetraethylorthosilicate reactant with a material having a formula $Si(OR)_4$ wherein each R is an alkyl group having 1, or 3-6 carbon atoms.

The above procedure can be modified by reacting from 1 to 4 moles of ascorbic acid or substitute ascorbic acid per mole of silicate ester, or by reacting 1 to 4 moles of silicate ester per each mole of ascorbic acid or substituted ascorbic acid to produce a product having from 2 weight percent, and more preferably from about 10 to about 15 weight percent silicon.

Following the general procedure as described above, the above modifications can be conducted by contacting the reactants for a time within the range of from about 1 to about 24 hours. The products of this invention can be used to treat disorders associated with bone tissue. More particularly, the products of this invention can be used to treat, prevent, or delay the onset of calcium-related bone disease. Thus, this invention comprises a method for the treatment of the aforesaid type of bone disorders, which comprises using the products of this invention. Thus, this invention comprises treatment of warm blooded vertebrates. Preferred species are man, and domesticated animals of economical importance, such as pets, draft animals, and animals raised to provide food. Thus, preferred vertebrates include birds, e.g. poultry, domesticated mammals such as house pets, and mammals of agricultural importance such as horses, cattle, swine, and sheep. The patient or animal being treated can have a therapeutic agent of this invention administered to it, in an amount of from about 0.1 to about 10 weight percent of the diet. Greater or lesser amounts can be used. Preferably, the therapeutic agents contain at least 2 and more preferably from about 10 to about 15 weight percent silicon. The therapeutic agent can be admixed with the diet, or when more convenient can be administered to the subject being treated in a unit dosage form.

The bone diseases susceptible to treatment with the products of this invention include tibial dyschondroplasia and other related diseases in poultry, cattle, sheep, dogs, and swine. In poultry, tibial dyschondroplasia is characterized by the failure to calcify the end of the growing tibia. It is thought that this is the same disease which occurs in mammals and which is known as osteochondrosis. Furthermore, this invention is useful in treating osteoporosis, especially post-menopausal osteoporosis in human females.

Thus, this invention comprises use of the above-described products of this invention in the treatment of animals, including man. As a preferred embodiment, this invention comprises a method of increasing the bone strength of an animal having a bone strength lower than desired, said method comprising administering to said animal a small, effective amount of a product produced by reacting ascorbic acid, or a substituted ascorbic acid, with a silicate ester such as a tetraalkylorthosilicate as described above.

As another preferred embodiment, this invention also comprises a method of treating calcium-related bone disorder in an animal having a calcium-related bone disorder, said method comprising administering to said animal a small, effective amount of a product produced by reacting ascorbic acid, or a substituted ascorbic acid, with a silicate ester such as a tetraalkylorthosilicate as described above.

To use the materials of this invention to treat bone disorders, one or more of the materials is administered in a small but effective amount, to the patient or animal being treated. Preferably, the product of this invention is administered orally. The product of the invention can be administered in the diet of the person or animal being treated, or it can be administered separate from the diet, e.g. in unit dosage form. Preferred unit dosage forms are tablets and capsules.

For treating poultry, a poultry feed containing from about 0.01 to 5 weight percent of a product of this invention can be used. Similar or lesser amounts can be used when treating other animal species, e.g. swine, cattle, sheep, and dogs. If it is desired to administer the product apart from the diet, an effective amount of product can be administered in tablets or capsules, or some other acceptable dosage form. Such unit dosage forms can be administered at multiple times during the day in order to help maintain an effective concentration of the active agent over the entire daily period. Preferably, the product of this invention used in treatment of bone disorders will have a silicon content of from about 10 to about 15 weight percent silicon. Products with greater or lesser silicon contents can be used.

Above, it was mentioned that the silicon-containing reaction products of this invention can be used in treating calcium-related bone disease in poultry. For this invention the term "poultry" includes all domestic fowl, namely chickens, turkeys, ducks, geese, and the like.

Corn is the principal diet for most poultry (at least in the United States of America and other countries where corn is a major grain crop). In such countries, a feed formulation comprising the following is desirable:

|  | Weight Percent |
| --- | --- |
| corn | 50–75 |
| soybean meal | 10–30 |
| calcium carbonate | 4–10 |
| product of this invention | 0.25–4.0 |

A typical feed preparation for large scale laying hen operations comprises the following by weight percent:

| | |
| --- | --- |
| Corn | 62–68 |
| Soy Bean Meal | 18–24 |
| Limestone | 5–9 |
| Alfalfa Meal | 1 |
| Phosphates | 2 |
| Sand | 1–2 |
| Vitamins, Amino Acids | |
| Salt and Other Minerals | 0–1 |

In countries where corn is not a principle crop, other grains can be substituted for the corn used in the aforementioned formulations.

Calcium carbonate is usually in the form of natural limestone ground to a suitable particle size, but sometimes oyster shells which have also been suitably ground, are used.

It can appreciated that a wide variety of nutrients or foods may be included in the diets of layers, or poultry laying hens. In a controlled environment, the hens are only exposed to desired foods or food products. A typical laying ration composition contains the following:

| | | Weight Percent |
| --- | --- | --- |
| crude protein | not less than | 16.0 |
| crude fat | not less than | 2.5 |
| crude fiber | not more than | 7.0 |
| calcium (as Ca) | not less than | 3.1 |
| calcium (as Ca) | not more than | 4.1 |
| phosphorus (P) | not less than | 0.5 |
| iodine (I) | not less than | 0.0001 |
| salt (NaCl) | not less than | 0.3 |
| salt (NaCl) | not more than | 0.9 |

The foregoing composition may be obtained from or include the following ingredients:

Grain and processed grain by-products. Includes corn, corn hominy, corn germ meal, barley, millet, oats, rice, rice hulls, rye, sorghum, wheat and wheat shorts. These are among the energy conferring ingredients, mostly carbohydrates with some proteins Plant protein products. Includes soybean oil meal, barley malt sprouts, coconut meal, corn distillers grain, corn gluten meal, cottonseed meal, pea seed, potato meal, peanut meal, rape seed meal, sunflower meal, wheat germ meal, brewers, yeast. All of these are protein sources.

Roughage or fiber. Includes dehydrated alfalfa, alfalfa hay, alfalfa leaf meal and pasture grasses. These are all fiber sources.

Animal and fish by-products. Includes blood meal, blood flour, dried buttermilk, dried whey, dried casein, fish meal, dried fish solubles, liver meal, meat meal, meat meal tankage, bone meal and dried skim milk. Anchovies, herring and menhaden are sources of fish meal. These products are protein sources.

Minerals and synthetic trace ingredients. Includes vitamins such as B-12, A, pantothenate, niacin, riboflavin, K, etc., DL methionine, choline chloride, folic acid, dicalcium phosphate, magnesium sulfate, potassium sulfate, calcium carbonate (limestone, oyster shells), salt, sodium selenite, manganous oxide, calcium iodate, copper oxide, zinc oxide and D activated animal sterol.

Molasses and animal fats are added to improve palatability and to increase or balance the energy levels.

Preservatives are also added such as, Ethoxyquin TM and sodium sulfite.

In general, a feed composition of this invention for laying hens should preferably contain, by weight percent, the following:

| | | Weight Percent |
| --- | --- | --- |
| crude protein | - at least about | 14 |
| crude fat | - at least about | 2 |
| crude fiber | - not more than about | 7 |
| calcium | - about | 2.7 to 4.1 |
| phosphorous | - at least about | 0.05 |
| iodine | - at least | 0.0001 |
| sodium | - about | 0.1 to 0.4 |
| chlorine | - about | 0.04 to 0.10 |
| reaction product of this invention | - about | 0.25 to 4.0 |

Similar diets can be used with poultry grown as sources of meat, i.e. broilers.

As stated above, when used to combat bone disease, the products of this invention can be administered in unit dosage forms, such as tablets or capsules. Other dosage forms are coated tablets, dragees, powders, and the like, and sustained release formulations with known sustained release agents. For such dosage forms, the active ingredients provided by this invention can be formulated with pharmaceutically acceptable adjuvants and carriers which are commonly used with some medicinal products. This invention comprises such pharmaceutical mixtures, and their use in combating bone disease.

Unit dosage forms of this invention conveniently contain 20 mg. to 1000 mg., of an active agent of this invention. They are generally administered from once a day to six time per day, preferably 2–4 times.

In an embodiment of this invention, the active ingredients described above may be formulated with an acidifying agent. Such acidifying agents are disclosed within application Ser. No. 153,456, filed Feb. 8, 1988, for Zeolite Compositions. Both of us, with another, are co-inventors of that related application. The disclosure within that application relating to acidifying agents, is incorporated by reference herein as if fully set forth.

As disclosed in application Ser. No. 153,456, the acidifying agent may be a pharmaceutically acceptable organic acid. Amino acids such as L-aspartic acid and glutamic acid can be used in this invention. Unlike glycine and similar acids in which each carboxyl group has an amino group on an alpha carbon, aspartic and glutamic acid has a carboxyl group which does not have an alpha amino group. This isolated carboxyl is non-zwitterionic, and therefor L-aspartic acid and similar materials with an isolated carboxyl comprise a preferred class of organic acids. The acid may be ascorbic acid, or some other acidic substance in which the acid function is derived from groups or radicals other than the carboxylic acid group. Alternatively, the acid may be a monobasic, dibasic, tribasic or tetrabasic carboxylic acid. Acids of this type include acetic acid, trimethylacetic acid, lactic acid, benzoic acid, malonic acid, tartaric acid, gluconic acid, citric acid, and the like. Preferably, the acid has three to six carbons such as propionic, pivalic, malic, malonic, maleic, succinic, butyric, valeric, fumaric and glutaric acids.

Thus, the acids employed in this invention may be selected from acids having one of the following formulas: $R'—COOH, R''(COOH)_2$, and $R'''(COOH)_3$. In these molecular formulas $R'$, $R''$ and $R'''$ are organic radicals, e.g. hydrocarbyl radicals, i.e. radicals which are solely composed of carbon and hydrogen. The radicals represented by $R'$, $R''$ and $R'''$ may be cyclic or acyclic, straight or branched chain, saturated or unsaturated. The cyclic radicals may be aromatic or non-aromatic. In the above formulas, the radicals $R'$, $R''$, and $R'''$ may also be selected from hydroxy-substituted hydrocarbyl radicals. Preferably, the acids contain up to about 10 carbon atoms.

The exact nature or molecular configuration of the acid selected is not critical so long as the acid is appreciably soluble in gastric fluid in the animal being treated and is pharmaceutically acceptable.

The acids may contain other elements than carbon, hydrogen and oxygen; they may contain a halogen, e.g. fluorine, chlorine or bromine, or sulphur, phosphorus and the like.

Other examples of acids that may be used include decanoic, undecylenic, salicylic, benzenesulfonic, camphor-sulfonic, p-chlorobenzensulfonic, 4-methylbicyclo[2.2.2]oct-2-ene-1-carboxylic, cyclopentanepropionic, 1,2-ethanedisulfonic, ethanesulfonic, o-(4-hydroxybenzyl)benzoic, 2-hydroxyethanesulfonic, methanesulfonic, dodecylsulfonic, stearic, 2-naphthylenesulfonic, 3-phenylpropionic, p-toluenesulfonic, gluconic, pantothenic, palmitic, hippuric, mandelic, and caproic acid, and the like. Inorganic acids such as hydrochloric, hydrofluoric, hydrobromic, sulfuric, orthophosphoric, boric acid and the like can also be used. Liquid acids are formulated in a delivery system which substantially prevents interaction of the acid and zeolite prior to ingestion. The solid acids also are preferably formulated according to the skill within the art, to reduce interaction of the components prior to ingestion.

This invention also comprises use of anhydrides which yield acids upon hydrolysis. Thus, acetic anhydride, pyrophosphates, and other similar simple and mixed anhydrides may be used in this invention. Useful anhydrides may be derived from the acids mentioned above.

Acidic salts are another type of acidifying agent utilizable in this invention. Such salts are typically salts of the above acids in which the cation is a weak base. Typical cations of this type are calcium, magnesium, ammonium, and the like. The exact nature of the cation is not critical so long as it does not cause an untoward effect when the salt is administered to the organism being treated according to this invention. The cation should be a weak enough base so that a pH achieved by adding the salt to an aqueous system can lower the pH to a value appreciably below 7. More particularly, salts which give a pH of 5 or lower when one gram molecular weight of the salt is added to a liter of distilled water are preferred. Salts which can be utilized as acidifying agents of this invention are exemplified by sodium hydrogen sulfate, potassium dihydrogen phosphate, calcium dihydrogen phosphate, calcium hydrogen phosphate, tricalcium phosphate, calcium sulfate, calcium hydrogen sulfate, the magnesium analogs of these salts, and the like, e.g. other acid phosphates and sulfates of the type named above.

The hydrochloric acid secreted by the gastric mucosa of the animal being treated does not comprise the acidic component of the compositions of this invention. Thus, for example compositions of this invention which include hydrochloric acid include that acid admixed with the efficacious active ingredient prior to administration to the patient or animal being treated.

The compositions of this invention comprise an appreciable amount of acidifying agent. For example, the compositions may contain from about 5 to about 75 weight percent acidifying agent and from about 95 to about 25 percent of the active ingredient of this invention. Compositions somewhat outside this range are also included within this invention. Preferably, compositions of this invention comprise from about 35 to about 65 weight percent acidifying agent and from about 65 to about 35 weight percent of our active ingredient.

The exact nature of the mechanism of therapeutic action of the products of this invention is not known. The product of the invention may or may not be absorbed per se from the gastrointestinal tract of the subject being treated. Thus, the efficacious action of the products of this invention in combating bone disorders may involve the breakdown of the products of this invention to one or more reactive species which are absorbed and transported to active sites in the body, e.g. osteoid tissue.

This invention has been described above by referring to products made by reacting a monosilicate compound with ascorbic acid or an ascorbic acid derivative. A skilled practitioner will recognize that similar materials can be made from silicon-containing compounds which have a plurality of silicon atoms within a molecule. Thus, for example, products of this invention can be made from oligosilicates, or polysilicates. Furthermore, products of this invention can be made by reacting ascorbic acid or an ascorbic acid derivative with one or more mixed silicates such as silicophosphates, borosilicates, and silicocarboxylates.

A skilled practitioner familiar with the above detailed description, can make many modifications or substitutions of this invention without departing from the scope and the spirit of the appended claims.

I claim:

1. A reaction product of ascorbic acid or a substituted ascorbic acid with a tetraorganosilicate, wherein said substituted ascorbic acid is substituted with a lower alkyl radical having up to about six carbon atoms and said tetraorganosilicate is a tetra-lower-alkyl silicate wherein said lower alkyls are alkyl radicals having from 1 to 5 carbon atoms.

2. The reaction product of claim 1 made from ascorbic acid and said tetraorganosilicate.

3. The reaction product of claim 2 wherein said tetraorganosilicate is tetraethylorthosilicate, $Si(OC_2H_5)_4$.

4. The reaction product of claim 3 containing from about 10 to about 15 weight percent silicon.

5. The reaction product of claim 1 prepared from a substituted ascorbic acid having up to about 12 carbon atoms, by reacting from about 1 to about 4 moles of substituted ascorbic acid per mole of silicate ester, or by reacting 1 to 4 moles of silicate ester per each mole of substituted ascorbic acid.

* * * * *